US010863910B2

(12) United States Patent
Brekken et al.

(10) Patent No.: US 10,863,910 B2
(45) Date of Patent: Dec. 15, 2020

(54) METHOD FOR DETECTING PULSATILE DYNAMICS OF THE OPTIC NERVE SHEATH, DIAGNOSTIC METHODS, MEDICAL USES, NON-INVASIVE MARKERS, SYSTEMS AND TRANSDUCER DEVICES

(71) Applicant: Nisonic AS, Trondheim (NO)

(72) Inventors: Reidar Brekken, Trondheim (NO); Tormod Selbekk, Trondheim (NO); Llewellyn Padayachy, Cape Town (ZA); Graham Fieggen, Rondebosch (ZA)

(73) Assignee: Nisonic AS, Trondheim (NO)

( * ) Notice: Subject to any disclaimer, the term of this patent is extended or adjusted under 35 U.S.C. 154(b) by 359 days.

(21) Appl. No.: 15/578,048

(22) PCT Filed: May 27, 2016

(86) PCT No.: PCT/EP2016/062057
§ 371 (c)(1),
(2) Date: Nov. 29, 2017

(87) PCT Pub. No.: WO2016/193168
PCT Pub. Date: Dec. 8, 2016

(65) Prior Publication Data
US 2018/0132739 A1 May 17, 2018

(30) Foreign Application Priority Data
May 29, 2015 (NO) .................................. 20150687

(51) Int. Cl.
A61B 5/03 (2006.01)
A61B 5/055 (2006.01)
(Continued)

(52) U.S. Cl.
CPC ............ A61B 5/031 (2013.01); A61B 5/0042 (2013.01); A61B 5/0066 (2013.01); A61B 5/024 (2013.01);
(Continued)

(58) Field of Classification Search
CPC ..... A61B 5/0042; A61B 5/0066; A61B 5/024; A61B 5/031; A61B 5/055; A61B 5/08;
(Continued)

(56) References Cited

U.S. PATENT DOCUMENTS 8,672,851 B1 3/2014 Quirk et al.
2005/0015009 A1 1/2005 Mourad et al.
(Continued)

FOREIGN PATENT DOCUMENTS

JP 2002-513310 A 5/2002
JP 2004-520870 A 7/2004
(Continued)

OTHER PUBLICATIONS

Bauerle, J., et al., Reproducibility and accuracy of optic nerve sheath diameter assessment using ultrasound compared to magnetic resonance imaging, BioMed Central Neurology, 13:187, 2013.
(Continued)

Primary Examiner — Michael T Rozanski
(74) Attorney, Agent, or Firm — Julie K. Staple; Dinsmore & Shohl LLP

(57) ABSTRACT

The invention relates to a new method, as well as diagnosis. A non-invasive marker, systems and equipment are also included.

6 Claims, 3 Drawing Sheets

(51) Int. Cl.
*A61B 8/00* (2006.01)
*A61B 6/03* (2006.01)
*A61B 5/00* (2006.01)
*A61B 5/024* (2006.01)
*A61B 5/08* (2006.01)
*A61B 6/00* (2006.01)
*A61B 8/08* (2006.01)
*A61B 8/02* (2006.01)
*A61B 8/10* (2006.01)

(52) U.S. Cl.
CPC ............ *A61B 5/055* (2013.01); *A61B 5/08* (2013.01); *A61B 5/7257* (2013.01); *A61B 5/7278* (2013.01); *A61B 6/032* (2013.01); *A61B 6/501* (2013.01); *A61B 6/503* (2013.01); *A61B 6/5217* (2013.01); *A61B 8/02* (2013.01); *A61B 8/10* (2013.01); *A61B 8/4488* (2013.01); *A61B 8/485* (2013.01); *A61B 8/5223* (2013.01); *A61B 8/0808* (2013.01); *A61B 8/5207* (2013.01); *A61B 8/543* (2013.01)

(58) Field of Classification Search
CPC ..... A61B 5/7257; A61B 5/7278; A61B 6/032; A61B 6/501; A61B 6/503; A61B 6/5217; A61B 8/02; A61B 8/0808; A61B 8/10; A61B 8/4488; A61B 8/485; A61B 8/5207; A61B 8/5223; A61B 8/543
See application file for complete search history.

(56) References Cited

U.S. PATENT DOCUMENTS

| | | |
|---|---|---|
| 2009/0192389 A1 | 7/2009 | Eilers et al. |
| 2010/0004537 A1 | 1/2010 | Eilers et al. |
| 2011/0137182 A1 | 6/2011 | Bellezza et al. |
| 2013/0110692 A1 | 5/2013 | Nightengale et al. |
| 2017/0065193 A1 | 3/2017 | Yu et al. |

FOREIGN PATENT DOCUMENTS

| | | |
|---|---|---|
| JP | 2008-543352 A | 12/2008 |
| JP | 2009-112839 A | 5/2009 |
| JP | 2011-529744 A | 12/2011 |
| WO | WO-200243564 | 6/2002 |
| WO | WO-2014160116 | 10/2014 |

OTHER PUBLICATIONS

Geeraets T., et al., Non-invasive assessment of intracranial pressure using ocular sonography in neurocritical care patients, Intensive Care Med, 34:2062-2067, 2008.

Hansen, H., et al., Dependence of the optic nerve sheath diameter on acutely applied subarachnoidal pressure—an experimental ultrasound study, Acta Ophthalmol, 89(6):526-532, Sep. 21, 2011.

Kim, J. et al., Dynamic optic nerve sheath diameter responses to short-term hyperventilation measured with sonography in patients under general anesthesia, Korean Janesthesiol, 67(4): 240-245, Oct. 2014.

Hansen, H. et al., Validation of the optic nerve sheath response to changing cerebrospinal fluid pressure: ultrasound findings during intrathecal infusion tests, J Neurosurg, 87(1): 34-40, 1997.

METHOD FOR DETECTING PULSATILE DYNAMICS OF THE OPTIC NERVE SHEATH, DIAGNOSTIC METHODS, MEDICAL USES, NON-INVASIVE MARKERS, SYSTEMS AND TRANSDUCER DEVICES

REFERENCE TO RELATED APPLICATIONS

This application is a U.S. national stage of PCT/EP2016/062057, filed May 27, 2016, which claims priority to Norway application No. NO20150687, filed May 29, 2015, the entire content of both of which is incorporated herein by reference.

TECHNICAL FIELD OF THE INVENTION

The invention relates to a new method, as well as diagnosis. A non-invasive marker, systems and equipment are also included.

BACKGROUND

Intracranial pressure (ICP) monitoring is an important tool in neurosurgery. ICP monitoring, both instantaneous pressure as well as for changes in pressure, provides important information on which to base medical and surgical treatment. This may be critical for patients with head injuries, stroke edema or acute intracranial haemorrhage. Elevated levels of intracranial pressure may inhibit supply of blood to the brain and cause tissue damage. Left untreated elevated intracranial pressure may be fatal. Rapid detection of raised ICP in patients with head trauma may prove critical for physicians and first aiders to reduce death and disability by applying the best possible therapy.

The gold standard for monitoring ICP remains invasive methods, using microsensor devices placed within the brain parenchyma or transduced external ventricular drains. These techniques provide valuable diagnostic information, but have specific limitations, the most significant of these being the risk of infection and hemorrhage.

The indications for ICP monitoring beyond some of the guidelines for severe traumatic brain injury still remain unclear (Rosenberg 2011). This results in unnecessary invasive procedures being performed, and highlights the need for a reliable non-invasive technique to estimate ICP. Numerous non-invasive surrogate markers of ICP have been described (Rosenberg 2011, Kristianson 2013, Beau 2014), but none of these have yet been able to replace invasive monitoring as the criterion standard technique.

One of the surrogate markers for ICP proposed is measurement of the diameter of the optic nerve sheath (ONS). It has been shown previously that the retrobulbar segment of the ONS is distensible and therefore dilates when ICP is increased (Hansen 1996, Geeraerts 2008). The technique of optic nerve sheath diameter (ONSD) measurement has gained steady support as a non-invasive surrogate marker of raised ICP. However, measurement of the ONSD does not yet provide an accurate assessment of ICP, largely because the optimal cutoff point for the ONSD measurement in patients with normal versus raised ICP varies considerably (Dubourg 2011). Thus, the relationship between ICP and optic nerve sheath diameter (ONSD) is not suitable as an accurate diagnostic tool for detection of raised ICP.

The static diameter at different time points with subsequent comparison of individual measurements has been investigated (Kim 2014, Driessen 2012, Singleton 2014), but to date no indication of the dynamic imaging of the ONS over the cardiac cycle to assess in-vivo dynamic characteristics of the ONS have been described. In WO 02/43564, a relation between intracranial volume and ICP is suggested. Here it is briefly suggested that the stiffness and/or compliance of central nervous system tissue is related to ICP. However, no experimental data exist exploring this relationship.

Thus, still to date we depend on unnecessary invasive procedures' being performed, which highlights the need for a reliable non-invasive technique to estimate ICP.

The inventors have surprisingly found that raised intracranial pressure (ICP) leads to a stiffer optic nerve sheath (ONS), resulting in changes in the dynamics in ONS and the surrounding tissue. This alteration is detectable by studying the ONS response to cardiovascular pulsation using transorbital ultrasound. As the gold standard of monitoring ICP is by invasive measurements associated with risk of infection and haemorrhage, the invention represents a technical advantage over prior art.

SUMMARY OF THE INVENTION

The invention discloses a method for detecting the pulsatile dynamics of the optic nerve sheath, ONS, or in a region surrounding ONS. In one embodiment, the region surrounding the ONS is the intraorbital and/or the intracanalicular region.

Accordingly, the invention is a method comprising the step of locating the optic nerve sheath, ONS, choosing one or more locations in the ONS or in the region surrounding the ONS, for example on each side of the ONS, and measure the pulsatile dynamic or displacement at said location over a given time period, for example over one heart cycle. By applying this method the invention provides a means for assessing ICP in a non-invasive matter. In one embodiment, the pulsatile dynamic is detected by a transducer device. A transducer device may comprise an ultrasound transducer, an x-ray emitter, a magnetic resonance imager, a computed tomography scanner, optical coherence tomography scanner or any combination thereof.

The invention uses a transducer device, such as ultrasound, in a method for diagnosing increased or decreased ICP by detecting the pulsatile dynamics of the ONS.

In one embodiment, the method for detecting pulsatile dynamics comprises the step of performing a Fourier analysis of the motion pattern in any given direction. In one particular embodiment, the motion pattern perpendicular to the ONS is analyzed. The pulsatile dynamic may be measured over a given time period or frequency, such as for example over the cardiac cycle.

In yet another embodiment, the method for detecting pulsatile dynamics comprises the step of obtaining the pulsatile dynamics by detecting displacement at two locations around the optic nerve sheath or in the region surrounding the and obtaining a parameter of deformability (Δ). The parameter of deformability may be calculated according to the equation (1):

$$\Delta = \frac{|d_A - d_B|}{d_A + d_B} \tag{1}$$

wherein ($d_A$) and ($d_B$) represents the displacement at each location around the ONS.

According to one embodiment, the method of the invention may in addition comprise the step of inducing a displacement or an associated biological response in order to obtain the pulsatile dynamics in the region surrounding the optic nerve sheath (ONS). Further, the method may in addition comprise the step of obtaining the optic nerve sheath diameter as an augment.

The invention also comprises use of a transducer device, such as transducer device comprising an ultrasound transducer, an x-ray emitter, a magnetic resonance imager, a computed tomography scanner, optical coherence tomography scanner or any combination thereof, in a method for diagnosing increased or decreased ICP by detecting the pulsatile dynamics of the ONS.

As described herein, the pulsatile dynamics may be obtained by detecting displacement at two locations around the optic nerve sheath and further obtain the parameter of deformability ($\Delta$), wherein the parameter is calculated according to the equation (1).

The use according to the invention in a method for diagnosing increased or decreased ICP may in addition comprise the step of obtaining the optic nerve sheath diameter.

The invention is an individual diagnostic marker for increased or decreased ICP, such as a non-invasive marker for raised ICP, obtained by assessing the pulsatile dynamic or displacement in any given direction over ONS. In particular a novel non-invasive marker of increased or decreased ICP is obtained by measuring the transverse pulsatile dynamic or displacement on both sides of the ONS. The marker may optionally in addition be based on the optic nerve sheath diameter measurement The present invention also provides an ICP assessment system. This system comprises a first device configured to detect, in a subject, the optic nerve sheath; a second device configured to obtain, from a subject, information of the pulsatile dynamics of the ONS; and the system further configured to, based on the pulsatile dynamics calculate the parameter of deformability in order to assess the subject's intracranial pressure.

Further, one embodiment of the invention is a handheld transducer device for detecting pulsatile dynamics in ONS or the area surrounding ONS. In one particular embodiment such a transducer is able to calculate a parameter of deformability, and optionally also obtain the ONS diameter.

A method for analyzing dynamic properties of the ONS using a transducer device is also provided, as well as a method of non-invasively assessing intracranial pressure (ICP) by detecting pulsatile dynamics of the optic nerve sheath (ONS) or in the area surrounding ONS.

Included in the scope of the invention is also a handheld transducer device, such as portable ultrasound equipment with analytic software, wherein the device may detect the pulsatile dynamics in ONS or the surrounding area. This provides the potential for safe, inexpensive monitoring, bedside or even pre-hospital measurements of ICP, e.g. in case of trauma.

In one particular embodiment the method of the invention include the steps of:
using transorbital ultrasound for assessing motion of tissue surrounding the ONS, wherein
the motion is assessed by choosing two points in equal depths on each side of the ONS, and then applying cross-correlation to find the best match of the area around these points from frame to frame over at least one heart cycles;
the transverse motion components (perpendicular to the ONS) are extracted;
Fourier analysis is applied to study the frequency components of this motion; and
the frequency corresponding to the cardiovascular pulsation is extracted.

dA and dB denotes the final displacement of each location around the ONS and represent the fundamental cardiac frequency component of the motion perpendicular to the ONS. According to the invention, the absolute difference in motion between the two locations, normalized by the sum of displacements, is used as a measure of dynamic behavior according to the equation:

$$\Delta = \frac{|d_A - d_B|}{d_A + d_B}$$

$\Delta$ is herein referred to as a parameter of deformability or deformability index, and represents a quantifiable means to measure the dynamic behaviour of the ONS and the surrounding tissue.

DETAILED DESCRIPTION OF THE INVENTION

Figure 1:
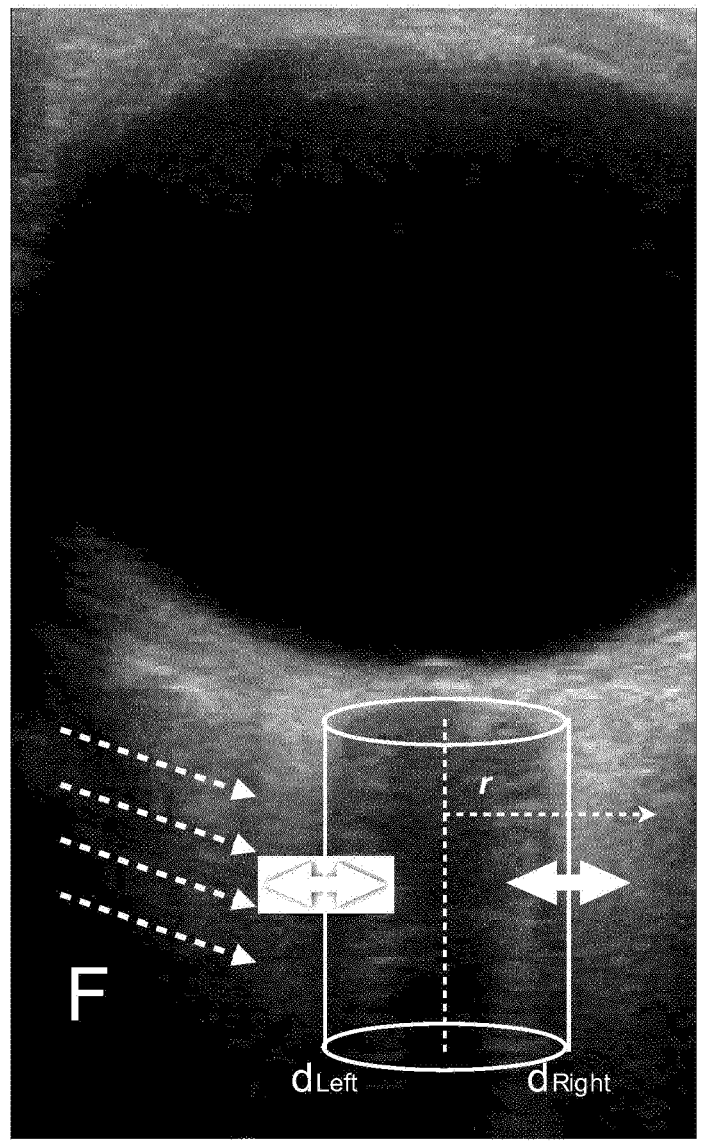
FIG. 1 shows how the optic nerve sheath (ONS) is subject to a modeled net force F due to cardiovascular pulsation (e.g. caused by internal or external arteries, or by pulsations transmitted through the CSF). This force causes a motion $d_{Left}$ on the left side of the ONS and a motion $d_{Right}$ on the right side. Raised ICP makes the ONS stiffer, which is observed as more equal radial (r) motion on each side of the ONS.

The present invention may be understood more readily by reference to the following detailed description taken in connection with the accompanying figures and example, which form a part of this disclosure. It is to be understood that the present invention is not limited to the specific devices, methods, applications, conditions, systems or parameters described and/or shown herein, and that the terminology used herein is for the purpose of describing particular embodiments by way of example only and is not intended to be limiting of the claimed invention.

The optic nerve is a bundle of individual axons that in turn connect the retinal ganglion cells to the brain. The optic nerve leaves the posterior of the eye at the scleral canal and travels to the optic chiasm.

The optic nerve is a second cranial nerve. It is about 5 cm in length, and it starts from the optic disc and extends up to the optic chiasma where the two nerves (from each eye) meet. The optic nerve has 4 parts:

1) the intraocular part is approximately 1 mm and it passes through the sclera, choroid and appears in the eye as the optic disc.

2) the intraorbital part is 30 mm and extends from the back of the eyeball to the optic foramina.

3) the intracanalicular part is 6 mm, and enters the optic canal through the optic foramen.

4) the intracranial part is 10 mm, and lies above the cavernous sinus. The optic chiasma is formed just above the sellae.

Both the intraorbital and the intracanalicular part of the optic nerve is surrounded by 3 layers of meninges; the pia, the arachnoid and dura mater. In contrast, the optic nerve in the cranial cavity is surrounded only by the pia mater. Between the dura and the arachnoid mater, is the subdural space and between arachnoid and pia is the subarachnoid space, both of which are communicating with the corresponding intracranial space.

The "optic nerve sheat, ONS" is hereinafter defined as the three layers of meninges; the pia mater, the arachnoid mater and the dura mater, surrounding the intraorbital and intracanalicular part of the optic nerve.

The "intraorbital region" is hereinafter defined as the region where the intraorbital part of the optic nerve lays.

The "intracanalicular region" is hereinafter defined as the region where the intracanalicular part of the optic nerve lays.

The optic nerve sheath surrounds the optic nerve, and encloses cerebrospinal fluid (CSF). An increase in cerebrospinal fluid pressure (which is equivalent to intracranial pressure) causes a distention of the optic nerve sheath (ONS).

According to one embodiment of the method of the invention, the region suitable for detection of the pulsatile dynamics is the ONS and the surrounding region, also known as the intraorbital and/or intracanalicular region The inventors have found that the increased intracranial pressure, and subsequent distension in the subarachnoid space, also leads to a stiffer and less compressible nerve sheath. This is due to the fact that the optic nerve sheath (ONS) is a continuation of the intracranial meninges, and the perineural subarachnoid space surrounding the optic nerve is a septated, trabeculated, cerebrospinal fluid (CSF) filled region. This space is in communication with the intracranial compartment, and changes in ICP are therefore transmitted along these CSF pathways. Consequently, as the ICP increases, a buildup of CSF occurs within the perineural space, leading to increased pressure and distension of the ONS. The inventors have found that the buildup of CSF within the perineural space, in addition to lead to the distension of ONS, also changes the dynamic of the optic nerve sheath and the tissue the surrounding regions. This is contrary to prior art which teaches ONS diameter measurement based on the distension as the sole marker of increased ICP. By assessing the dynamics, the inventors have developed a new, reliable method. This method provides an accurate diagnostic tool, useful both in relation to assessing ICP and other condition which affects the optic nerve sheath.

The invention discloses a method for detecting the pulsatile dynamics of ONS and pulsatile dynamics in tissue in regions surrounding ONS. In particular, the invention discloses a method for detecting pulsatile dynamics of ONS and in the surrounding tissue in the optic canal, such as in the intraorbital region and/or intracanalicular region. Particularly, it is provided a method for detecting the pulsatile dynamics of ONS and in the region surrounding the ONS comprising the step of a) locating the ONS, b) choosing one or more location in the ONS or the intraorbital and/or intracanalicular region surrounding the optic nerve sheath and c) measure the pulsatile dynamic at the location over a given time period or frequency. Alternatively the method comprises the step of a) locating the ONS, b) using a transducer device to detect motion and/or displacement and/or velocity for tissue selected around the optic nerve sheath, c) considering the difference in behaviour for detected motion and/or displacement and/or velocity for one or at least two locations around the ONS, The method is particularly useful in order to assess the intracranial pressure, as a relation between ICP and the increased pressure within the subarachnoid space in the ONS is established by this invention. However, assessment of ONS dynamics may also serve as an indicator for other conditions than ICP. Examples can be cancerous tumor in the optic nerve, optic nerve disorders such as optic neuritis or inflammation, glaucoma, ischemic optic neuropathy, or other damage to the optic nerve or surrounding tissue.

The term "pulsatile dynamic" as used herein refers to the motion, movement, displacement or changes in velocity, or any parameters derived thereof. As such 'pulsatile dynamics' could mean any relevant dynamic property. While 'pulsatile' indicates that the parameter is preferably related to cyclic behaviour such as that imposed by respiratory or cardiovascular pulsation, the concept should not be understood as limited to cyclic behaviour. The pulsatile nature of the dynamics may be caused directly by the arterial pulsation, or transmission of pulsatility (e.g. variation in pressure) through the CSF. The pulsatility may be caused by the cardiac or respiratory cycles, among other. It is also possible that a periodic alteration of behavior of the optic nerve sheat may be caused by external factors, as for example by applying mechanical or acoustic force.

The estimated dynamics may be related directly or indirectly to ICP, because of the increased levels of CSF in the perineural space.

By analyzing this dynamics the inventors were able to show an association with ICP. Thus, they have provided a tool for diagnosing increased levels of ICP. The invention discloses a method for analyzing dynamic properties of the ONS using a transducer device, in particular by using transorbital ultrasound transducer. This method provides an insight into the relationship between ONS dynamics in response to variations in the ICP.

Specifically, the inventors have found that raised ICP alters the dynamics in or in the region surrounding the ONS, and that this alteration may be detected by studying the motion, movement, displacement or changes in velocity (e.g. the dynamic behaviour) of the ONS or surrounding structures. By using the transducer device the inventors have been able to further investigate this pulsatile dynamics of the ONS over a given time period (e.g. a cardiac cycle).

The expression "a given time period" as used herein refers to the length in time of the cardiac cycle, the respiratory cycle or any other time interval, time period or corresponding frequency that is suitable for observation of the dynamics of the ONS and the surrounding tissue, or able to influence the dynamics of the ONS. The pulsatile dynamics may according to the present invention be determined over a period of time corresponding to for example one cardiac cycle. If at least two location surrounding ONS is chosen, the given time period used may be the same or different for each location. That is, measurement for one location may be done in one given time period, and for another location in a later time period.

The term "transducer device" as described herein refers to devices comprising an ultrasound transducer, an x-ray emitter, a magnetic resonance imager, a computed tomography scanner, optical coherence tomography scanner or any combination thereof. The transducer device may be used to obtain an image of the optical nerve sheath and the surrounding tissue/structure, making it possible to quantify the pulsatile dynamics of the relevant tissue. Transducer devices also include similar technology to obtain relevant measurements without displaying images.

The expression "in the region surrounding ONS" as used herein refers to the ONS nearby tissue or structure surrounding the ONS that is influenced by the increased levels of CSF in the perineural space in the same or similar way as the ONS itself is influenced, or alternatively influenced by the ICP in a comparable fashion. The expressions "region surrounding" and "area surrounding" are used interchangeably. The region may be the intraorbital or the intracanalicular region.

The invention represents a novel approach, which adds insight into the factors involved in alteration of the ONS in response to changes in ICP. As such, the invention is a new method of detecting characteristics related to ICP by obtaining information about movement or displacement of the ONS or the surrounding structure. The movement/displacement/velocity may be collected by B-mode ultrasound or other imaging modalities (e.g., ocular coherence tomography) or by other means known to those skilled in the art.

The invention includes use of transorbital ultrasound to detect the pulsatile dynamics of the ONS. This quantifiable dynamics may be used as an individual diagnostic marker for increased or decreased ICP.

The invention is based on the observation that cardiovascular pulsation (i.e. caused directly by arterial pulsation, or transmission of pulsatility through the CSF) leads to motion of the ONS. Based on the observation that the ONS becomes stiffer and less compliant with increasing ICP, the inventors found that the transverse motion (i.e. perpendicular to the ONS) is more equal on each side of the nerve with high ICP compared to normal ICP. As exemplified by the invention, this may be quantified by the absolute difference between the transverse pulsatile displacements on the left and right side of the ONS, normalized by the sum of displacements. Thus, the invention provides a method for quantifying the displacement by calculating the parameter of deformability, $\Delta$:

$$\Delta = \frac{|d_A - d_B|}{d_A + d_B} \quad (1)$$

The value of this parameter indicates how much the ONS deforms during cardiovascular pulsation, and is therefore interpreted physically as a measure of deformability. The parameter of deformability may also be referred to as the deformability index. The deformability index or parameter of deformability may be calculated based on movement/displacement in the ONS and the surrounding tissue, caused by the increased level of CSF in the perineural space, by various means known to the skilled person.

Since the ability to deform is inversely related to stiffness, the inventors have found that this parameter is smaller in a high ICP group compared to a normal ICP group. In fact, a significant difference was noted between patient groups with high versus normal ICP, supporting the invention as a relevant non-invasive marker of raised ICP. Thus, the invention discloses a novel non-invasive marker of increased or decreased ICP obtained by measuring the pulsatile dynamics in two locations in the area surrounding the ONS, such as in the intraorbital and/or intracanalicular region. The invention includes a method of measuring transverse pulsatile displacement on both sides of the ONS in these regions. Increased ICP leads to increased stiffness (i.e. reduced deformability) of the nerve sheath, thus making an objective and quantifiable new approach for assessing variations in ICP.

The parameter of deformability may be derived from analyses of the dynamic behavior of ONS or surrounding tissue within a given time interval, that may be used for assessing ICP. The dynamic information may also be combined in different ways, and is not restricted to the derivations in Eq. 1.

The term "locations" as used herein refers to points or region-of-interest (ROI) of any shape and size in the area surrounding the ONS. In Eq. 1 these locations are represented by $d_A$ and $d_B$. The terms "point", "location" and "region of interest" are used interchangeably. In the example and figures enclosed in this description, $d_A$ is sometimes also denoted $d_{Left}$, and $d_B$ is sometimes also denoted $d_{Right}$.

The term "assessing ICP", as used herein, refers to the detection or determination or monitoring of both increased or decreased and normal levels of intracranial pressure. It also includes the method of (continuously) monitoring the ICP levels, and thus detecting potential changes in the ICP.

The most important finding in this study is the significant difference between the deformability of the ONS in the group with high ICP compared to the group with normal ICP, thus clearly supporting the technical effect of the invention. This finding may be applied in all cases where ONS dynamics are quantifiably changed in response to variations in the ICP, indifferent on the method used to quantify it. An element of importance is that the improvement provided by the present invention compared to the prior art lays in the observation that the natural biovariation of the ONS dynamics between individuals in the different patient groups is less than that observed in mere diameter analysis.

Thus the invention includes a method for analyzing dynamic properties of the ONS using a transducer device. Further a method of detecting ONS dynamics in response to ICP and/or variations in the ICP is provided. A method of detecting variations in the ICP by continuously measuring the pulsatile dynamics of the ONS is accordingly also provided.

The motion/displacement/velocity in tissue selected around the optic nerve sheath may be detected in any given direction, whether it is transvers motion perpendicular to the ONS or it is motion or displacement detectable longitudinal to the ONS, or any other direction.

In the past the non-invasive assessment of ICP has been dependent of the ONS diameter measurement. This method is highly unreliable. It has been considerably variation in the optimal cutoff point for the ONSD measurement. The noted variation in ONSD between studies is likely due to a more complex relationship between the ONS and ICP. The magnitude of ONS distension caused by the increase in pressure within the subarachnoid space is dependent on a variety of factors, including the degree to which ICP is increased, the rapidity of the increase in ICP and the elastic characteristics of the ONS. All these factors influence the capability for distension and retraction of the ONS. In addition, the relationship between ONSD and ICP is not known for every individual case. This is because of natural biovariation between individuals in normal optic nerve diameter and in tissue mechanical elasticity. Naturally ONS diameter measurements alone do not provide reliable estimates of ICP. The invention is thus also useful as an augment to the interpretation of the more familiar ONS diameter measurement. In their study, the inventors have found that the pulsatile forces from the beating of the heart deform the ONS dynamically during the cardiac cycle. This is in contrast to the former absolute distention related to the increased pressure within the ONS. By using a transducer device over the oculus, the invention as described herein may be used complementary to the static measurements of ONSD.

By using an imaging transducer device it is possible to combine the information from analysis of pulsatile dynamics and diameter of the ONS. Thus the combined information, which may be obtained during the same examination as presented by this invention, represents an improvement of the overall accuracy and reliability of examining the ONS as a non-invasive marker of ICP.

Thus the new approach provides additional information complementary to the ONSD. The invention contributes to an overall improvement in assessing the ONS in cases of suspected increased ICP, both as an individual marker and by augmenting the interpretation of ONSD measurements. The concept of pulsatile dynamics of the ONS, obtainable by using the method as described herein, thus improve the specificity compared to ONSD alone, making it possible to differentiate between pathologically distended ONS due to raised ICP and widened ONS not related to raised ICP.

The invention also includes the analysis of additional information, e.g. longitudinal motion or phase content of the Fourier transform (e.g. delay between motions at different location around the nerve). It is also possible to apply the herein described method in relation to other motion components than the fundamental heart rate frequency. In addition to higher harmonics of the cardiac frequency, respiration is an example of another physiological process that causes a periodic motion in the body tissues. Motion or dynamics, preferably but not limited to pulsatile or periodic of nature, might also be applied by the use of externally applied mechanical or acoustic force of any magnitude, or artificially induced as a response to other stimuli, e.g. medication, or electrical or audiovisual impulses.

The invention include a method for assessment of intracranial pressure, or any parameters related to intracranial pressure, in particular comprising the step of transmitting ultrasound through the oculus using an adequate transducer and ultrasound scanner and calculation of motion in the ultrasound data (preferable selected around the oculus and optic nerve sheet complex). Further the method according to the present invention is analysing the spectrum of the calculated motion that has occurred during the given time period by doing Fourier analysis of the motion pattern in any given direction. The invention uses the characteristics of the spectral component of the motion for any one or at least two region of interests to derive a parameter, such as the parameter of deformability.

Also disclosed are a method of non-invasively monitoring ICP, comprising the step of locating the ONS, using an imaging device, like for instance transorbital ultrasound, to detect motion/displacement/velocity for tissue selected around the optic nerve sheath, considering the difference in behaviour for detected motion/displacement/velocity for one or at least two locations or regions of interests, in order to assess the intracranial pressure.

The invention uses a transducer to investigate the pulsatile dynamics of the ONS over a cardiac cycle.

The invention discloses a method for assessment of ONS pulsatile dynamics using transorbital ultrasound imaging.

The invention is a novel method for analyzing the pulsatile dynamic properties of the ONS using transorbital ultrasound imaging.

The invention include any method for estimating parameter(s) related to displacement/motion at the heart beat frequency or period, or any other that is occurring during any time sequence and any spectral component for one or at least two different regions of interests in the acquired ultrasound data. The region of interest (ROI) can be of any given size.

The invention is a novel method for extracting dynamic characteristics (e.g. pulsatile motion) of the optic nerve sheath or nearby structures, for the purpose of assessing intracranial pressure. According to the method the pulsatile dynamic is measured based on the detection of motion or velocity from data obtained from the transducer device. The method comprises the step of obtaining dynamic measurements of ROI in or close to the ONS by e.g imaging, such as ultrasound, tracking and/or estimating motion (e.g. alternatively crosscorrelation), extracting different motion components, such as e.g. perpendicular to the ONS, on both sides of the ONS, with or without need for filtering to enhance relevant (here: pulsatile→cardiovascular) motion, e.g. extracting motion corresponding to heart-rate frequency and relating the motion to ICP by using the parameter of deformability. The present invention also provides devices to be applied in such a method. In one embodiment the device includes an imaging component configured to obtain an image of the optic nerve sheath and the related tissue, and based on the detected motion in this region of interest produce an assessment of the ONS deformation during the cardiovascular pulsation.

FIG. 1 illustrates that the optic nerve sheath (ONS) is subject to a modeled net force F due to cardiovascular pulsation (e.g. caused by internal or external arteries, or by pulsations transmitted through the CSF). This force causes a motion $d_{Left}$ on the left side of the ONS and a motion $d_{Right}$ on the right side. Raised ICP makes the ONS stiffer, which is observed as a more equal radial motion on each side of the ONS.

Figure 2A:
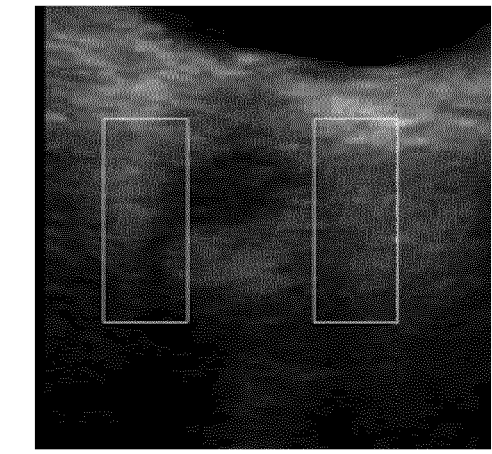
FIGS. 2A and 2B illustrate the image processing, with a normal (FIG. 2A) and a high ICP patient (FIG. 2B). Upper row: The white squares show the region of interest used for tracking. Mid row: radial displacement as a function of time (vertical axis) after extraction of the motion component corresponding to the heart rate frequency. Note that the curves are strongly zoomed in compared to the images in the upper row (the squares are 25 pixels wide, pulsation is approx. 0.1 pixel). Lower row: the same curves, plotted together, with displacement amplitude along the vertical axis and time along the horizontal axis. Note the difference in displacements for the normal ICP patient compared to the high ICP patient.
Figure 2A:
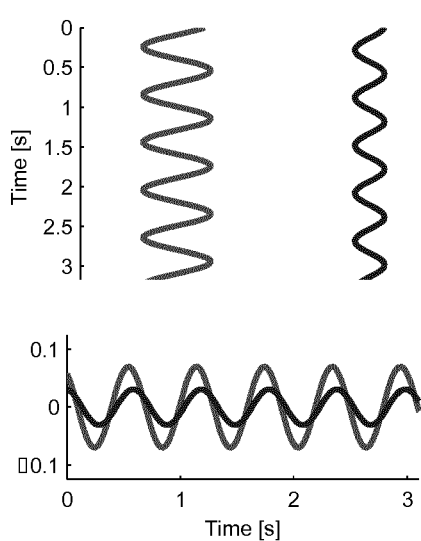
Figure 2B:
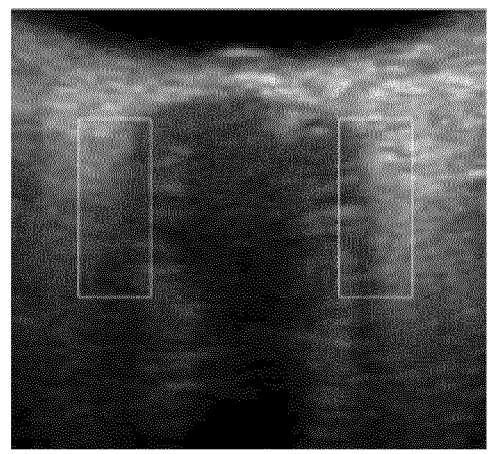
Figure 2B:
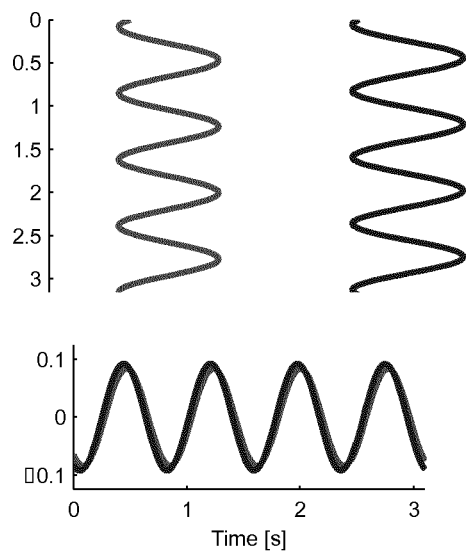

FIGS. 2A and 2B illustrate the image processing, with a normal FIG. 2A and a high ICP patient FIG. 2B. Upper row: The white squares show the region of interest used for tracking. Mid row: radial displacement as a function of time (vertical axis) after extraction of the motion component corresponding to the heart rate frequency. Note that the curves are strongly zoomed in compared to the images in the upper row (the squares are 25 pixels wide, pulsation is approx. 0.1 pixel). Lower row: the same curves, plotted together, with displacement amplitude along the vertical axis and time along the horizontal axis. Note the difference in displacements for the normal ICP patient compared to the high ICP patient.

Figure 3:
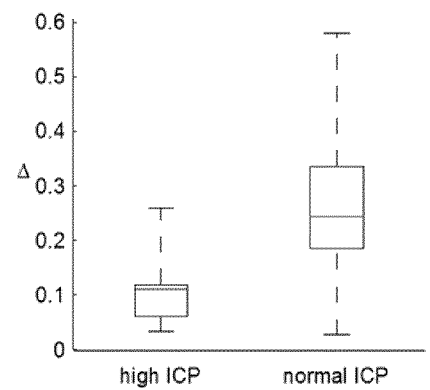
FIG. 3 is a boxplot illustrating the difference in radial (or transverse) pulsatile deformability (parameter of deformability), $\Delta$, between the two groups. The boxplot shows median, 25- and 75-percentiles and range.

FIG. 3 is a boxplot illustrating the difference in radial (or transverse) pulsatile deformability (parameter of deformability), Δ between the two groups. The boxplot shows median, 25- and 75-percentiles and range.

Figure 4:
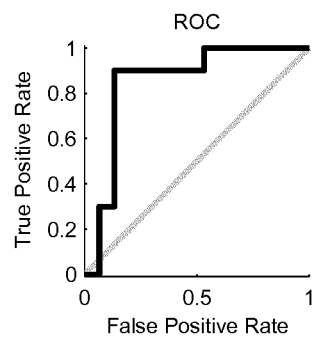
FIG. 4 represents a receiver operator curve. Area under curve (AUC) was 0.85.

FIG. 4 shows receiver operator curve. Area under curve (AUC) was 0.85.

Figure 5:
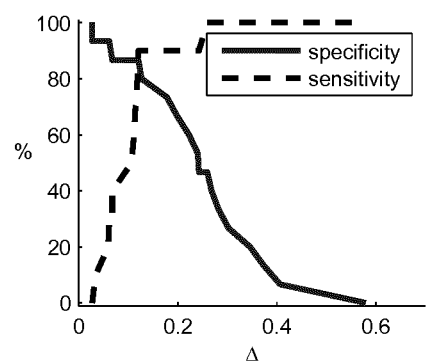
FIG. 5 shows sensitivity and specificity as a function of $\Delta$. A cutoff of $\Delta=0.121$ gave sensitivity 90% and specificity 87%.

FIG. 5 shows sensitivity and specificity as a function of Δ. A cutoff of Δ=0.121 gave sensitivity 90% and specificity 87%.

Example 1

Patients

We performed an exploratory research study, retrospectively analyzing data from 16 patients (age≤12 years old), managed at the Red Cross War Memorial Children's Hospital (Cape Town, South Africa). Inclusion criteria were that: 1) invasive ICP measurement, via insertion of a parenchymal microsensor or a ventricular catheter, was performed during a diagnostic or therapeutic intervention, and 2) concurrent transorbital ultrasound images of the ONS were acquired. Patients with ocular pathology were excluded. The human research ethics committee of the University of Cape Town and the research committee of the Red Cross War Memorial Children's Hospital approved the study, and informed consent was obtained for all patients enrolled in the study. The demographic details are listed in Table I.

TABLE I

Demographic data.

| Patient | Age (months) | Gender | Heart rate (bpm) | Diagnosis | ICP (mmHg) | Group |
|---|---|---|---|---|---|---|
| A | 120 | M | 78 | Posterior fossa Tumor | 28 | High |
| B | 116 | F | 103 | Hydrocephalus | 33 | High |
| C | 132 | M | 168 | Trauma | 32 | High |
| D | 33 | M | 117 | Posterior fossa Tumor | 37 | High |
| E | 24 | F | 92 | Hemispheral tumor | 20 | High |
| F | 124 | F | 112 | Hydrocephalus | 30 | High |
| G | 38 | F | 69 | Hydrocephalus | 26 | High |
| H | 44 | M | 134 | Hydrocephalus | 36 | High |
| I | 36 | M | 100 | Tethered cord | 10 | Normal |
| J | 9 | M | 150 | Hydrocephalus | 8 | Normal |
| K | 72 | F | 92 | Chiari1 malformation | 5 | Normal |
| L | 54 | M | 102 | Spinal dysraphism | 10 | Normal |
| M | 144 | M | 80 | Hydrocephalus | 10 | Normal |
| N | 10 | M | 120 | Hydrocephalus | 11 | Normal |
| O | 8 | M | 130 | Hydrocephalus | 10 | Normal |
| P | 94 | M | 103 | Trauma | 10 | Normal |

Image Acquisition

A single investigator experienced in the use of transorbital ultrasonography acquired ultrasound images from both eyes, using a 15 MHz linear array probe (L15-7io, Philips, Bothell, USA). The images were acquired after the patients were intubated and ventilated, just prior to insertion of the invasive ICP monitor. The heart rate was recorded, and ultrasound acquisition was performed when the hemodynamic parameters were stable. The image depth varied from 3 to 5 cm, and spatial image resolution from 0.06 to 0.11 mm per pixel. The duration of each image sequence was 5 to 10 seconds, and the temporal resolution varied from 40 to 56 frames per second.

Image Processing

The objective of the image processing was to exploit the high temporal resolution of the ultrasound images for analyzing motion related to cardiovascular pulsation on each side of the optic nerve sheath. The approach is explained in FIGS. 2A and 2B, and in the following text.

$1^{st}$ Step: Tracking

Tracking was initialized by manually selecting a point at similar depths on both sides of the ONS in the first frame of each image sequence. The motion was then automatically tracked over the entire sequence using normalized two-dimensional cross-correlation from frame to frame for a region of interest (25 by 61 pixels) around the selected points. The ultrasound data were interpolated, and parabolic approximation was applied to the correlation matrix for sub-pixel motion estimation. The motion component in the horizontal image direction (i.e. radial, or perpendicular, to the nerve) was extracted for further analysis.

$2^{nd}$ Step: Fourier Analysis

To extract the motion that was related to the cardiovascular pulsation, we applied Fourier analysis to obtain the frequency components of the radial motion. The amplitude of the (fundamental) frequency component corresponding to the heart rate of each patient was extracted for the left and right side of the ONS in each dataset, yielding the radial pulsatile displacements $d_{Left}$ and $d_{Right}$, respectively.

The algorithm was implemented in Matlab (MathWorks, Natick, Mass., USA).

Data Analysis and Statistics

Since the data were retrospectively analyzed, we expected some out-of-plane motion, which is known to deteriorate correlation-based tracking. Each dataset were therefore graded by one blinded operator on a scale from 0-2:

Grade 0: steady acquisition, barely perceivable probe movement

Grade 1: perceivable probe motion, no loss of ONS appearance

Grade 2: distinct probe movement, with some loss of ONS appearance

Seven datasets scoring grade 2 were excluded, leaving 25 for further analysis.

The motion analysis was run five times for the left and right side of the optic nerve sheath for each dataset to account for variability due to the manual initialization of the tracking region. The mean of the five displacement values was used as the motion estimate, and the variation was quantified using pooled standard deviation.

The 25 datasets were split into a high ICP group (≥20 mmHg), and a normal ICP group (<20 mmHg), comprising 10 and 15 datasets, respectively. Δ was calculated using equation (1), and one-sided Mann-Whitney U-test was used to statistically compare the two groups. Diagnostic accuracy was investigated using receiver operating characteristic (ROC).

Results

A total of 25 datasets were analyzed. The radial pulsatile displacement at each side of the ONS was assessed five times for each dataset. The mean displacement was 8.3, with a pooled standard deviation of 0.54, measured in percentage of a pixel.

The radial pulsatile deformability (parameter of deformability) was calculated for each dataset. The median was $\Delta=0.11$ for the high ICP group, compared to $\Delta=0.24$ for the normal ICP group (p=0.002). FIG. 3 shows a boxplot illustrating the median and spread for each group. Results for each patient are included in Table II.

TABLE II

Results. Datasets with out-of-plane motion given a grade 2 were excluded from the analysis. Radial displacements $d_{Left}$ and $d_{Right}$ were measured in percentage of a pixel.

| | | Left eye | | | | Right eye | | | |
|---|---|---|---|---|---|---|---|---|---|
| | | $d_{Left}$ | $d_{Right}$ | $\Delta$ | Grade | $d_{Left}$ | $d_{Right}$ | $\Delta$ | Grade |
| High ICP group | A | — | — | — | 2 | — | — | — | 2 |
| | B | 7.76 | 8.75 | 0.06 | 1 | 9.88 | 9.23 | 0.03 | 1 |
| | C | — | — | — | 2 | 2.73 | 3.42 | 0.11 | 1 |
| | D | 5.17 | 4.17 | 0.11 | 1 | — | — | — | 2 |
| | E | 15.37 | 13.58 | 0.06 | 0 | 13.74 | 17.44 | 0.12 | 1 |
| | F | 20.49 | 26.12 | 0.12 | 1 | — | — | — | 2 |
| | G | — | — | — | 2 | 11.22 | 9.79 | 0.07 | 1 |
| | H | 6.76 | 5.37 | 0.11 | 1 | 3.51 | 5.97 | 0.26* | 0 |
| Normal ICP group | I | 5.65 | 3.16 | 0.28 | 0 | 2.52 | 3.78 | 0.20 | 0 |
| | J | 4.01 | 1.83 | 0.37 | 1 | 5.70 | 3.63 | 0.22 | 0 |
| | K | 13.68 | 8.38 | 0.24 | 1 | 7.22 | 3.04 | 0.41 | 0 |
| | L | 7.98 | 4.60 | 0.27 | 1 | 9.12 | 11.78 | 0.13 | 0 |
| | M | 17.47 | 10.64 | 0.24 | 0 | — | — | — | 2 |
| | N | 5.20 | 3.62 | 0.18 | 0 | 1.52 | 5.69 | 0.58 | 1 |
| | O | 15.94 | 16.83 | 0.03* | 1 | 8.15 | 3.96 | 0.35 | 0 |
| | P | 4.90 | 5.61 | 0.07* | 0 | 5.52 | 10.32 | 0.30 | 1 |

*Values that are wrongly classified using a cut-off value of 0.121.

ROC analysis gave an area under curve (AUC) of 0.85 (95% CI: 0.61-0.97) (FIG. 4). FIG. 5 shows the sensitivity and specificity as a function of the parameter $\Delta$. Choosing a cut-off value at $\Delta=0.121$ would give a sensitivity of 90% and a specificity of 87%. 3 out of 25 (12%) datasets would be wrongly classified using this cut-off.

Conclusion

Example 1 illustrates the feasibility of non-invasive transorbital ultrasound for assessing optic nerve sheath pulsatile dynamics. The results demonstrate a significant difference between patient groups with high versus normal ICP, and thus support the technical effect of the invention. The inventors are the first to explore the relationship between radial pulsatile deformability (parameter of deformability) and intracranial pressure. The invention is relevant as a non-invasive marker of increased or decreased ICP, and may also serve to augment the interpretation of static ONSD measurement.

Example 2

A handheld transducer device, able to transmit and receive ultrasound is used to perform the method according to the present invention. The handheld device is placed in a suitable position for sonification of the ONS. The device is able to processes the received ultrasound to obtain information about the dynamics of the ONS or surrounding structures, and calculates a parameter of deformability based on the ONS dynamics. The dynamics is related to ICP. The result is then presented either as an image, curve or number on a display, or by other indicators such as sound or light signals. The parameter may in addition be a function including other physiological information, such as the diameter of the ONS or hemodynamic information.

Example 3

It is possible to measure the dynamics in only one location. The dynamics is then related to a reference value. Optionally the dynamics may also be related to some physiological parameters, e.g. blood pressure, or ECG. Without being bound by theory, it is assumed that higher (intracranial) pressure gives a faster transmission of (cardiovascular) pressure pulses, which could be observed as a smaller time delay between ECG and pulsatile displacement. This time delay could be measured as the phase difference in a cross-correlation between the ECG and the displacement obtained using the described methodology.

REFERENCES

Rosenberg J B, Shiloh A L, Savel R H, Eisen L A. Non-invasive methods of estimating intracranial pressure. *Neurocrit Care* 2011; 15: 599-608.

Kristiansson H, Nissborg E, Bartek Jr J, Andresen M, Reinstrup P, Romner B. Measuring elevated intracranial pressure through noninvasive methods: A review of the literature. *J Neurosurg Anesthesiol* 2013; 25: 372-85.

Beau B. Non-invasive assessment of cerebrospinal fluid pressure. *J Neuro-ophthalmol* 2014; 34: 288-94.

Hansen H C, Helmke K. The subarachnoid space surrounding the optic nerves. An ultrasound study of the optic nerve sheath. *Surg Radiol Anat* 1996; 18: 323-8.

Geeraerts T, Merceron S, Benhamou D, Vigue B, Duranteau J. Non-invasive assessment of intracranial pressure using ocular sonography in neurocritical care patients. *Intensive Care Med* 2008; 34: 2062-7.

Dubourg J, Javouhey E, Geeraerts T, Messerer M, Kassai B. Ultrasonography of optic nerve sheath diameter for detection of raised intracranial pressure: a systematic review and meta-analysis. *Intensive Care Med* 2011; 37: 1059-68.

Kim J Y, Min H G, Ha S I, Jeong H W, Seo H, Kim J U. Dynamic optic nerve sheath diameter responses to short-term hyperventilation measured with sonography in patients under general anesthesia. *Korean J Anesthesiol* 2014; 67: 240-5.

Driessen C, van Veelen M L, Lequin M, Joosten K F, Mathijssen I M. Nocturnal ultrasound measurements of optic nerve sheath diameter correlate with intracranial pressure in children with craniosynostosis. *Plast Reconstr Surg* 2012; 130: 448e-51e.

Singleton J, Dagan A, Edlow J A, Hoffmann B. Real-time optic nerve sheath diameter reduction measured with bedside ultrasound after therapeutic lumbar puncture in a patient with idiopathic intracranial hypertension. *Am J Emerg Med* 2014 Dec. 19. doi: 10.1016/j.ajem.2014.12.030. [Epub ahead of print].

WO 02/43564 A1

The invention claimed is:

1. A method for non-invasively calculating a marker indicating possibly increased intracranial pressure (ICP) of a patient, the method comprising:
using a transducer device to monitor displacement of an optic nerve sheath (ONS) of the patient at a first location on a first side of the ONS over a period of time and at a second location on a second side of the ONS over the period of time;

comparing the displacement of the ONS at the first location with the displacement of the ONS at the second location; and using the compared displacement of the ONS at the first location and at the second location to determine a measure of stiffness as a marker indicating possibly increased intracranial pressure (ICP) of the patient, wherein nearly equal displacement of the ONS at both the first and second locations corresponds to increased ONS stiffness and higher ICP compared to a normal individual.

2. The method as claimed in claim 1, wherein using a transducer device to monitor displacement of the ONS of the patient at the first location on the first side of the ONS over the period of time provides a measurement $d_A$ and using a transducer device to monitor displacement of the ONS of the patient at the second location on the second side of the ONS over the period of time provides a measurement $d_B$, and wherein a parameter of deformability ($\Delta$) is calculated according to the equation:

$$\Delta = \frac{|d_A - d_B|}{d_A + d_B}.$$

3. The method as claimed in claim 1, comprising performing a Fourier analysis of a motion pattern of the optic nerve sheath in a direction perpendicular to a longitudinal axis of the optic nerve sheath.

4. The method as claimed in claim 1, comprising inducing a displacement or an associated biological response in order to prompt motion of the optic nerve sheath.

5. The method as claimed in claim 1, further comprising obtaining the optic nerve sheath diameter.

6. A method as claimed in claim 1, wherein using a transducer device to monitor displacement comprises using an ultrasound transducer, an x-ray emitter, a magnetic resonance imager, a computed tomography scanner, optical coherence tomography scanner or a combination of any thereof.

* * * * *